(12) United States Patent
Leanna et al.

(10) Patent No.: US 9,538,903 B2
(45) Date of Patent: Jan. 10, 2017

(54) ENDOSCOPE ANCHORING DEVICE

(71) Applicant: Boston Scientific Scimed, Inc., Maple Grove, MN (US)

(72) Inventors: Gary Leanna, Holden, MA (US); Kurt Geitz, Sudbury, MA (US); Oscar R. Carrillo, Jr., Attleboro, MA (US); Kevin Richardson, Austin, TX (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 80 days.

(21) Appl. No.: 14/571,582

(22) Filed: Dec. 16, 2014

(65) Prior Publication Data

US 2015/0099931 A1    Apr. 9, 2015

Related U.S. Application Data

(63) Continuation of application No. 12/352,179, filed on Jan. 12, 2009, now abandoned.

(60) Provisional application No. 61/020,556, filed on Jan. 11, 2008.

(51) Int. Cl.
| | | |
|---|---|---|
| *A61B 1/04* | (2006.01) | |
| *A61B 1/00* | (2006.01) | |
| *A61B 1/005* | (2006.01) | |
| *A61B 17/00* | (2006.01) | |
| *A61B 17/34* | (2006.01) | |

(52) U.S. Cl.
CPC .......... *A61B 1/00082* (2013.01); *A61B 1/005* (2013.01); *A61B 1/00006* (2013.01); *A61B 1/00018* (2013.01); *A61B 1/00087* (2013.01); *A61B 1/00094* (2013.01); *A61B 1/00096* (2013.01); *A61B 1/00147* (2013.01); *A61B 17/00234* (2013.01); *A61B 2017/00778* (2013.01); *A61B 2017/00986* (2013.01); *A61B 2017/3488* (2013.01)

(58) Field of Classification Search
CPC .......... A61B 1/00094; A61B 1/00087; A61B 1/00089; A61B 1/00006; A61B 1/00096
USPC .......... 600/116, 127, 129; 604/118–120, 509
See application file for complete search history.

(56) References Cited

U.S. PATENT DOCUMENTS

| | | |
|---|---|---|
| 1,972,428 A | 9/1934 | Richard |
| 3,495,586 A | 2/1970 | Eberhard |
| 3,568,659 A | 3/1971 | Karnegis |
| 3,643,653 A | 2/1972 | Takahashi et al. |
| 4,608,965 A | 9/1986 | Anspach et al. |
| 4,699,611 A | 10/1987 | Bowden |
| 4,705,041 A | 11/1987 | Kim |
| 4,813,930 A | 3/1989 | Elliott |
| 5,071,412 A | 12/1991 | Noda |

(Continued)

FOREIGN PATENT DOCUMENTS

| | | |
|---|---|---|
| WO | WO 98/24372 | 6/1998 |
| WO | WO 98/32380 | 7/1998 |
| WO | WO 2005/104989 A2 | 11/2005 |

*Primary Examiner* — Timothy J Neal
(74) *Attorney, Agent, or Firm* — Bookoff McAndrews, PLLC

(57) ABSTRACT

A device for accessing tissue within a body lumen comprises an elongated body portion defining a lumen and an anchoring mechanism including an expanding structure on a distal portion of the elongated body portion. The anchoring mechanism moves the expanding structure from an insertion configuration in which the expanding structure is constricted against the device to an operative configuration in a body in which the expanding structure expands away from the device without altering a length of the anchoring mechanism in combination with a control mechanism for selectively engaging the anchoring mechanism.

20 Claims, 5 Drawing Sheets

(56) References Cited

U.S. PATENT DOCUMENTS

| | | |
|---|---|---|
| 5,354,302 A | 10/1994 | Ko |
| 5,547,469 A | 8/1996 | Rowland et al. |
| 5,558,620 A | 9/1996 | Heckele et al. |
| 5,730,726 A | 3/1998 | Klingenstein |
| 5,938,585 A | 8/1999 | Donofrio |
| 6,325,798 B1 | 12/2001 | Edwards et al. |
| 6,506,178 B1 | 1/2003 | Schubart et al. |
| 6,569,150 B2 | 5/2003 | Teague et al. |
| 6,607,476 B1 | 8/2003 | Barnhart |
| 6,645,160 B1 | 11/2003 | Heesch |
| 7,141,055 B2 | 11/2006 | Abrams et al. |
| 7,220,227 B2 | 5/2007 | Sasaki et al. |
| 7,238,182 B2 | 7/2007 | Swoyer et al. |
| 7,257,450 B2 | 8/2007 | Auth et al. |
| 7,306,614 B2 | 12/2007 | Weller et al. |
| 7,357,801 B2 | 4/2008 | Burbank et al. |
| 2004/0162485 A1 | 8/2004 | Wendlandt |
| 2004/0186349 A1 | 9/2004 | Ewers et al. |
| 2004/0204709 A1 | 10/2004 | Burbank et al. |
| 2004/0249362 A1 | 12/2004 | Levine et al. |
| 2005/0065506 A1 | 3/2005 | Phan |
| 2005/0182465 A1* | 8/2005 | Ness ............... A61B 17/3421 607/116 |
| 2006/0036218 A1 | 2/2006 | Goodson et al. |
| 2006/0069414 A1 | 3/2006 | Imran et al. |
| 2006/0178560 A1 | 8/2006 | Saadat et al. |
| 2006/0206148 A1 | 9/2006 | Khairkhahan et al. |
| 2007/0088203 A1* | 4/2007 | Lau ................. A61B 17/0218 600/205 |
| 2009/0192505 A1* | 7/2009 | Askew ............. A61B 18/0218 606/21 |

* cited by examiner

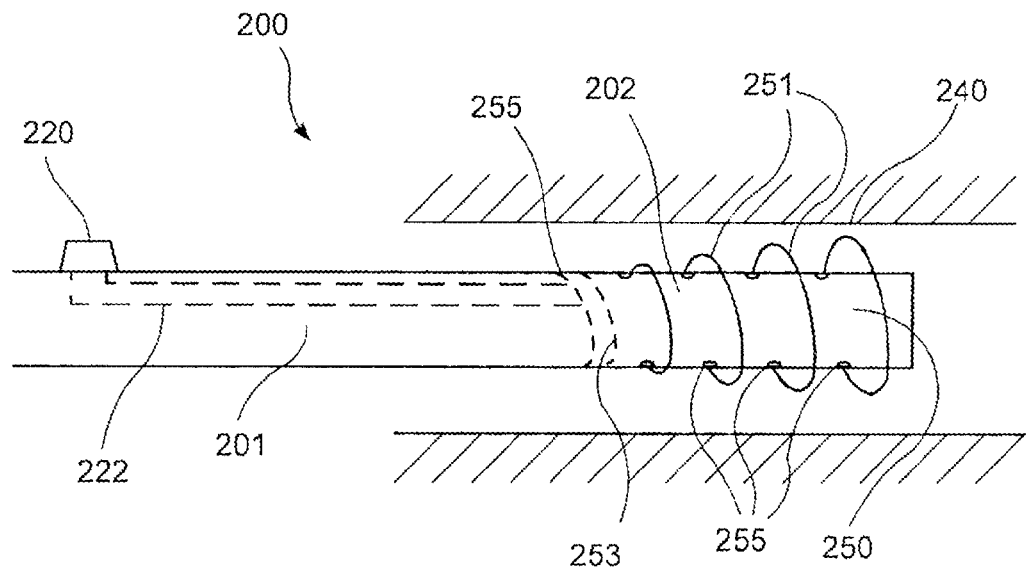
F I G. 3
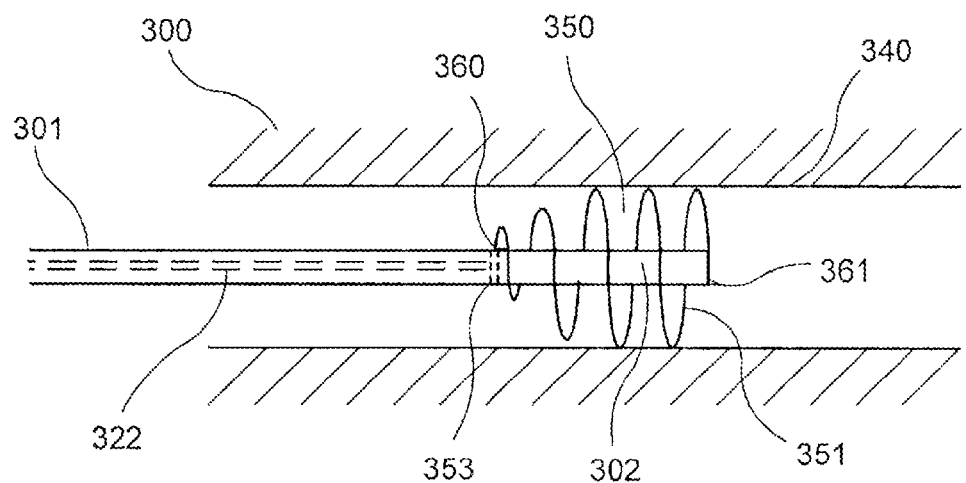
F I G. 4

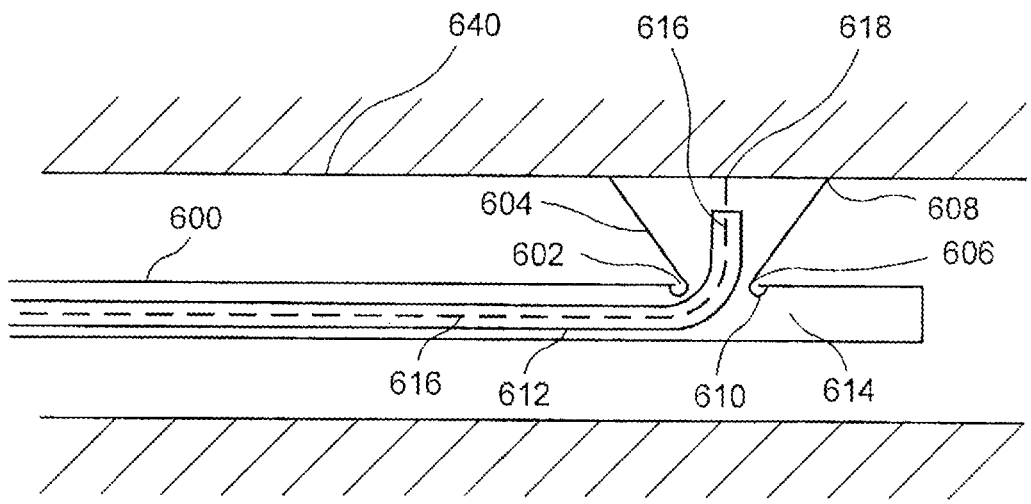
F I G. 8
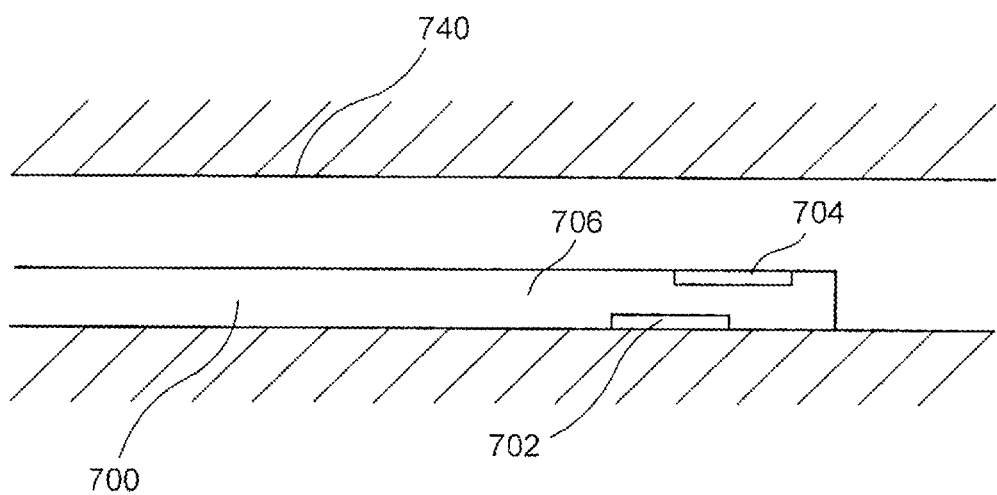
F I G. 9

ENDOSCOPE ANCHORING DEVICE

PRIORITY CLAIM

This application is a Continuation Application of U.S. patent application Ser. No. 12/352,179, filed Jan. 12, 2009, which claims the benefit under 35 U.S.C. 119(e) of U.S. Provisional Patent Application Ser. No. 61/020,556, filed Jan. 11, 2008, all of which are incorporated herein by reference.

BACKGROUND

Endoscopes are often inadvertently moved away from target locations within body lumens. This may result from forces accidentally applied to the endoscope, natural body motion, muscular activity (e.g., peristalsis) and/or resistances to the positioning of the endoscope accumulated during insertion. Such inadvertent movement of an endoscope relative to a target location may cause discomfort and/or trauma and may complicate and/or reduce the efficacy of the procedure.

SUMMARY OF THE INVENTION

The present invention is directed to a device for accessing tissue within a body lumen, the device comprising an elongated body portion defining a lumen and an anchoring mechanism including an expanding structure on a distal portion of the elongated body portion, the anchoring mechanism moving the expanding structure from an insertion configuration in which the expanding structure is constricted against the device to an operative configuration in a body in which the expanding structure expands away from the device without altering a length of the anchoring mechanism in combination with a control mechanism for selectively engaging the anchoring mechanism.

BRIEF DESCRIPTION OF THE DRAWINGS

FIG. 3 shows a side view of a device according to a third exemplary embodiment of the present invention in position within a body lumen;

FIG. 4 shows a side view of a device according to a fourth exemplary embodiment of the present invention in position within a body lumen;

FIG. 8 shows a side view of a device according to a seventh exemplary embodiment of the present invention in position within a body lumen; and FIG. 9 shows a side view of a device according to an eight exemplary embodiment of the present invention in position within a body lumen.

DETAILED DESCRIPTION

The present invention, which may be further understood with reference to the following description and the appended drawings, relates to devices and methods for securing endoscopes in desired positions within body lumens. For example, the present devices and methods may be used to secure an endoscope in a body lumen such as the duodenum, esophagus, large intestine, gastrointestinal tract, etc. It is submitted that, although the exemplary embodiments of the present invention are described with respect to particular lumens and procedures, they are not meant to limit the applicability of the present invention.

Devices and methods according to the present invention employ an endoscope provided with a gripping portion formed on a distal end thereof. It is noted that the use of the term distal herein refers to a direction away from a user of the device while the term proximal refers to a direction approaching the user of the device (e.g., a physician). Proximal portions of the devices disclosed herein remain external to the patient when in an operative position while distal portions of the device are inserted into the body, for example, via a naturally occurring orifice and one or more body lumens.

Figure 1:
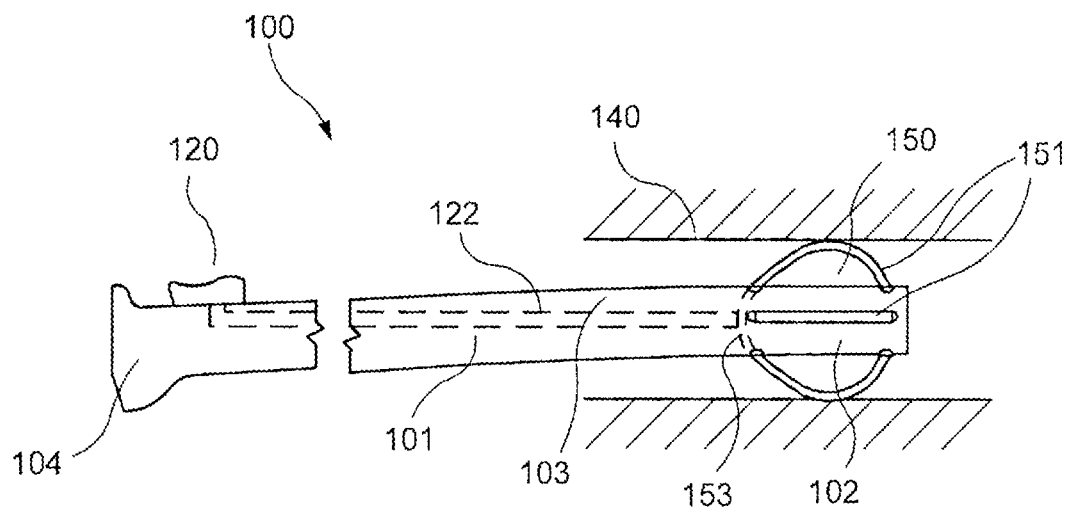
FIG. 1 shows a side view of a device according to a first exemplary embodiment of the present invention in position within a body lumen.

As shown in FIG. 1, a device 100 according to a first embodiment of the invention includes an endoscope 100 with an anchoring mechanism 150 formed on a distal end 102 thereof. The anchoring mechanism 150 engages tissue (e.g., lumenal tissue 140) to resist movement of the endoscope 101 relative thereto. In use, a user inserts the endoscope 101 through the lumen 140 to a target location. Those skilled in the art will understand that the target location is often specific to the procedure being performed and the anatomy of the individual patient and may, for example, be located using a vision system formed in the distal end 102 of the endoscope 101. As would be further understood by those skilled in the art, the endoscope 101 is preferably sufficiently flexible to conform to curvatures in the lumen 140 while maintaining a degree of longitudinal rigidity required to transmit to the distal end 102 forces applied to a proximal portion 104 to urge the endoscope 101 distally through the lumen 140 without bunching in the lumen 140.

The anchoring mechanism 150 includes a plurality of retractable ribs 151 coupled to an actuator 120 on a proximal end 104 of the endoscope 101 (i.e., formed on a portion of the endoscope 101 which remains accessible to the user throughout the procedure). The ribs 151 are preferably maintained in a retracted position in which they lie substantially flat along an outer surface 103 of the endoscope 101 to minimize a profile thereof during insertion and retraction of the endoscope through the lumen 140 to minimize trauma to lumenal tissue. Then, when the endoscope 101 has reached a desired location within the lumen 140 and it is desired to maintain the endoscope 101 in this position, the user operates the actuator 120 to move the ribs 151 away from this insertion configuration to a deployed configuration in which the ribs 151 extend radially outward from the outer surface 103 to frictionally engage the walls of the lumen 140. Proximal ends of the ribs 151 may, for example, be coupled to a ring 153 slidably mounted within the outer surface 103 while distal ends of the ribs 151 are fixed in place. In the insertion configuration, the ring 153 is withdrawn proximally so that the ribs 151 lay flat against the outer surface 103 of the endoscope 101. When the actuator 120 is operated to move the ribs 151 to the deployed configuration, the ring 153 is urged distally by, for example, a flexible pushing member 122 coupled between the ring 153 and the actuator 120. As the ring 153 moves distally, the ribs 151 are longitudinally compressed causing them to bow radially outward (e.g., via slots in the outer surface 103). The actuator 120 may then be locked in this position using any known mechanism (e.g., friction fit, ratchet mechanism, etc.) to maintain the anchoring mechanism 150 in the deployed configuration until the user wishes to remove the endoscope 101 or to move it to another location in the lumen 140. At this point, the user moves the actuator 120 to its original position allowing the anchoring mechanism 150 to return to the insertion configuration with the ribs 151 lying flat within slots in the outer surface 103. Those skilled in the art will understand that the anchoring mechanism may be moved from the deployed to the insertion configuration under a spring bias of the ribs 151, through the motion of the actuator 120 of via any other suitable known mechanism.

The bowed shape and lateral extent of the actuated ribs 151 is preferably selected to engage the walls of a lumen 140 with a desired force sufficient to hold the endoscope 101 in place in the lumen 140, as shown in the embodiment of FIG. 1, even when subjected to inadvertent forces of an expected magnitude. As would be understood by those skilled in the art, the pushing member 122 may be replaced by a system of filaments and pulleys to move the ring 153 proximally and distally as desired or by any other suitable mechanism or combination of mechanisms.

The ribs 151 preferably comprise a flexible, substantially biocompatible material (e.g., a plastic such as Polyetheretherketone ("PEEK"), polyimide, etc. or a metal such as Nitinol, stainless steel, etc.). Furthermore, the ribs 151 may be substantially equally dispersed about the circumference of the endoscope 101 to center the endoscope 101 within the lumen 140. Alternatively, as would be understood by those skilled in the art, if it is desired that a particular side of the endoscope 101 be located adjacent to a wall of the lumen 140, the ribs 151 may be sized appropriately around the endoscope 101 to achieve any desired position of the distal end 102 within the lumen 140.

Figure 2:
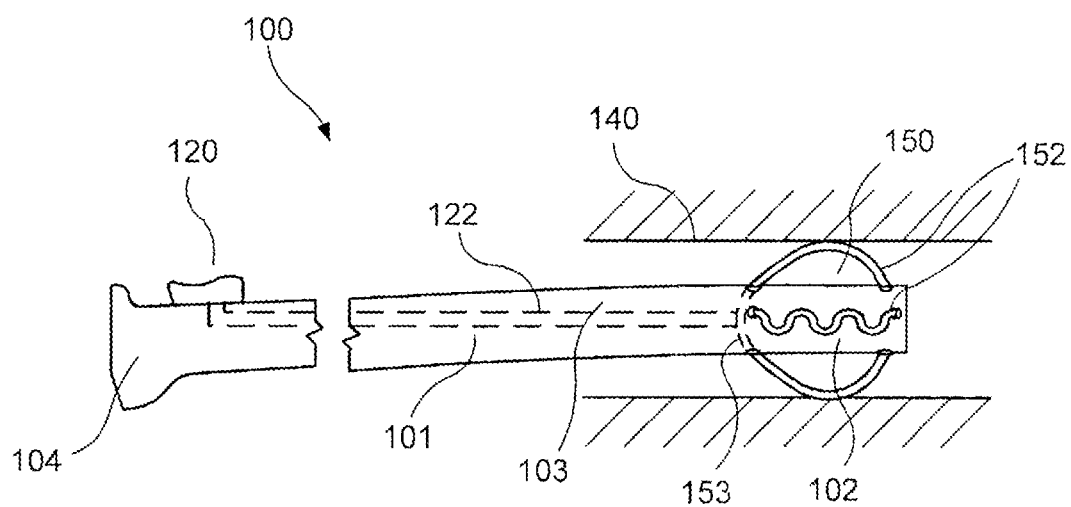
FIG. 2 shows a side view of a device according to a second exemplary embodiment of the present invention in position within a body lumen.

In addition, the length (extent parallel to a longitudinal axis of the endoscope 101) and width (extent perpendicular to the longitudinal axis) of each of the ribs 151 may be the same or, in the alternative, may vary to achieve any desired distribution of the anchoring force to the portions of the walls of the lumen 140. Furthermore, the contacting surface of each of the ribs 151 may be composed of a high friction material or, alternatively, the contacting surface may be a ribbed surface with a plurality of protrusions such as bumps to aid in gripping the walls of the lumen 140, as those skilled in the art will understand. Furthermore, the ribs 151 may be formed of different shapes and need not be formed in the arc shape shown in FIG. 1. For example, as shown in FIG. 2, the device 100 may comprise ribs 152 each of which contains a series of bends and curves along a longitudinal length thereof. As would be understood by those skilled in the art, the bends may increase a gripping force exerted thereby to the lumen 140. The design of the ribs 152 may comprise any plurality of bends and curves therein.

As described above, the endoscope 101 is inserted into the lumen 140 with the anchoring mechanism 150 in the insertion configuration (i.e., with the ribs 151 flat against the outer surface 103) to minimize trauma to the lumen 140. Once a user of the endoscope 101 has traversed the endoscope 101 to a target area, the actuator 120 is moved to a distal-most position, thereby engaging the ribs 151 with the walls of the lumen 140. The actuator 120 may further be provided with a locking feature or friction fit design to prevent the actuator 120 from sliding prematurely. When a designated procedure is complete, the actuator 120 may once again be retracted and the endoscope 101 may be removed from the lumen 140. Although the actuator 120 has been described as a slidable trigger, the actuator 120 may be triggered in any suitable manner (i.e., push-button trigger, etc.) without deviating from the spirit and scope of the present invention. Furthermore, it is noted that the device 100 may be sized to minimally obstruct a working channel of an endoscope, so as to allow ample space for tool delivery therethrough.

As shown in FIG. 3, a device 200 according to a second embodiment of the present invention includes an endoscope 201 which may be employed in a manner similar to that of the embodiment of FIG. 1. The endoscope 201 may be provided with an actuator 220 that may be used to retract and expand a anchoring mechanism 250 located on a distal end 202 thereof. The anchoring mechanism 250 comprises a series of flexible wires 251, each extending around a section of the distal end 202 of the endoscope 201. The flexible wires 251 may be formed of a wire material such as Nitinol or stainless steel which can withstand high amounts of elastic deformation before a permanent deformation sets in, as those skilled in the art will understand. Each of the flexible wires 251 extends out of a corresponding pair of holes 255 placed separated from one another around the circumference of the distal end 202 substantially equally positioned along the length of the endoscope 201. Each of the flexible wires 251 may be connected, by known means, to an internally located control cable or filament 222 extending to an actuator 220 on a proximal portion 204 of the endoscope 201. Each of the flexible wires 251 acts as a radial spring, wherein each loop of the flexible wires 251 may be connected to the control cable or filament 222.

As described above in regard to the endoscope 101, when the endoscope 201 is being traversed to a target area in the body, the anchoring mechanism 250 is maintained in an insertion configuration wherein each of the flexible wires 251 is constricted to fit snugly around a radial portion of the endoscope 201. Specifically, retraction of the control cable or filament via the actuator 220 may exert a force on each of the flexible wires 251, pulling a length of each of the flexible wires 251 into the endoscope 201 and causing the restriction of each of the flexible wires 251 against the endoscope 201. Once a target area has been reached, the user moves the actuator 220 distally to expand the flexible wire 251 radially outward to place a desired amount of pressure on the walls of the lumen 240, securing the endoscope 201 in place. Specifically, the actuation of the actuator 220 forces a length of each of the flexible wires 251 out of the endoscope 201, thereby increasing a radial length of each loop formed therein. The increased radial length of each of the loops made by the flexible wires 251 causes a radial expansion, thereby engaging the flexible wires 251 with the inner walls of a lumen. When the procedure has been completed, the user operates the actuator 220 to move the anchoring mechanism 250 to the insertion configuration to release the endoscope 201 for movement through the lumen 240 to a new target location or for removal from the body.

As shown in FIG. 4, a device 300 according to yet another embodiment of the present invention comprises an endoscope 301 with a anchoring mechanism 350 located on a distal end 302 thereof. As with the previously described embodiments, the anchoring mechanism 350 is withdrawn into an insertion configuration before the endoscope 301 is inserted into a lumen 340 and advanced therethrough. The anchoring mechanism 350 of the embodiment of FIG. 3 comprises a coil 351 extending around a portion of the distal end 302 of the endoscope 301. As would be understood by those skilled in the art the coil 351 may be formed of any suitable biocompatible material such as, for example, Nitinol, pre-formed stainless steel wire cables, similar to snare loop cables or polymers.

A proximal end of the coil 351 may be connected to a deploying mechanism which is, in turn, coupled to an actuator (not shown) as in the previous embodiments. The deploying mechanism may include, for example, a ring 353 coupled to the actuator via a cable or filament(s) 322 to move the anchoring mechanism 350 between the insertion configuration in which the wire 351 is snugly received around the distal end 302 of the endoscope 301 and a deployed configuration in which the wire 351 is radially expanded to engage tissue of the lumen 340 to anchor the distal end 302 in a target position. It may be particularly advantageous to employ a material with shape memory properties herein, as such a material can retain a deployment shape (i.e., an expanded coil shape) for an extended period of time while strained to a high level, such as in the insertion configuration, as detailed below. Actuation of the coil 351, which may exhibit shape memory properties as noted above, may be similar to that of the embodiment of FIG. 2. Specifically, actuation of a proximally located actuator (not shown) may cause the cable or filament 322 to move distally, thereby causing the coil 351 to expand radially and conform to the walls of the lumen 340. Conversely, a retraction of the actuator (not shown) may cause the cable or filament 322 to move proximally, thereby shortening the radial length of the coil 351 and causing a constriction of the coil 351 against the endoscope 301. As would be understood by those skilled in the art, the outer surface of the distal end 302 may include a recess within which the wire 351 may be received when in the insertion configuration so that the outer surface is substantially smooth. The wire 351 can extend out of a proximal slit 360 formed on the outer surface of the endoscope 301 and coils around the distal end 302 to a distal slit 361 through which the wire 351 re-enters the endoscope 301 to which the distal end of the wire 351 is attached, for example, via any known means such as bonding or welding. In an alternate embodiment, the wire 351 may be attached to a component such as a ring, which is, in turn, attached or releasably attached to the endoscope 301.

As would be understood by those skilled in the art, the size and shape of the wire 351 is preferably selected so that a desired anchoring force is applied to the tissue of the lumen 340 (i.e., a desired frictional engagement is established between the endoscope 301, and the surrounding tissue) when the anchoring mechanism is in the deployed configuration. The wire 351 may be formed, for example, as a substantially planar ribbon with a surface that may be textured or otherwise treated or coated to enhance the frictional engagement of the surrounding tissue. In these cases, the endoscope 301 may include an optional cover which, when in the insertion configuration, eliminates contact between the wire 351 and the surrounding tissue. The wire 351 may have a cross-section that is substantially circular, elliptical, triangular, square, or of any other desired shape. The employment of cross sectional shapes other than round, smooth shapes provides corners or edges that may aid in anchoring the wire 351 in the body and provide an additional locking force thereto. Additionally, the surface of the wire may be smooth or ribbed with a plurality of protrusions to increase the gripping ability of the anchoring mechanism 350.

Figure 5:
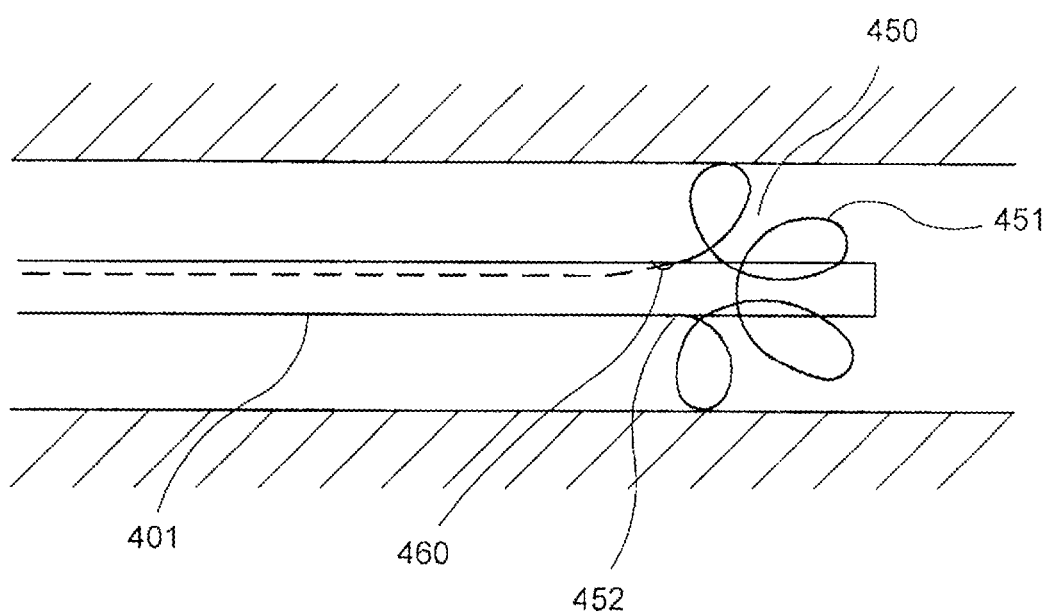
FIG. 5 shows a side view of a device according to a fifth exemplary embodiment of the present invention in position within a body lumen.

In a further embodiment of the present invention, as shown in FIG. 5, the anchoring mechanism 450 comprises a flexible wire 451 which is formed as a unitary element with a cable or filament extending through an endoscope 401. A distal end of the anchoring wire 451 may be attached to a joint portion 452 on the endoscope 401 while a proximal end of the anchoring wire 451 may be connected to an actuator (not shown) located on a proximal portion of the endoscope 401. The anchoring wire 451 may span the longitudinal length of the endoscope 401 and extend therefrom via an opening or slit 460 located on a distal length. A distal length of the anchoring wire 451, which is comprised of a shape memory material such as Nitinol, may be shape memorized in a shape such as a series of petals or a series of bends which expand radially outward from the endoscope 401 when actuated. Those skilled in the art will understand that the anchoring wire 451 may move into its memorized shape through the application of heat, through the action of body heat, by applying a small electrical jolt thereto. Alternately, the anchoring wire 451 may run alongside a portion of the outer body of the endoscope 401, wherein the wire 451 may be joined to the endoscope 401 along a distal length thereof with length of the joint portion 452 being indicative of a longitudinal length of the anchoring portion of the anchoring mechanism 450.

Figure 6:
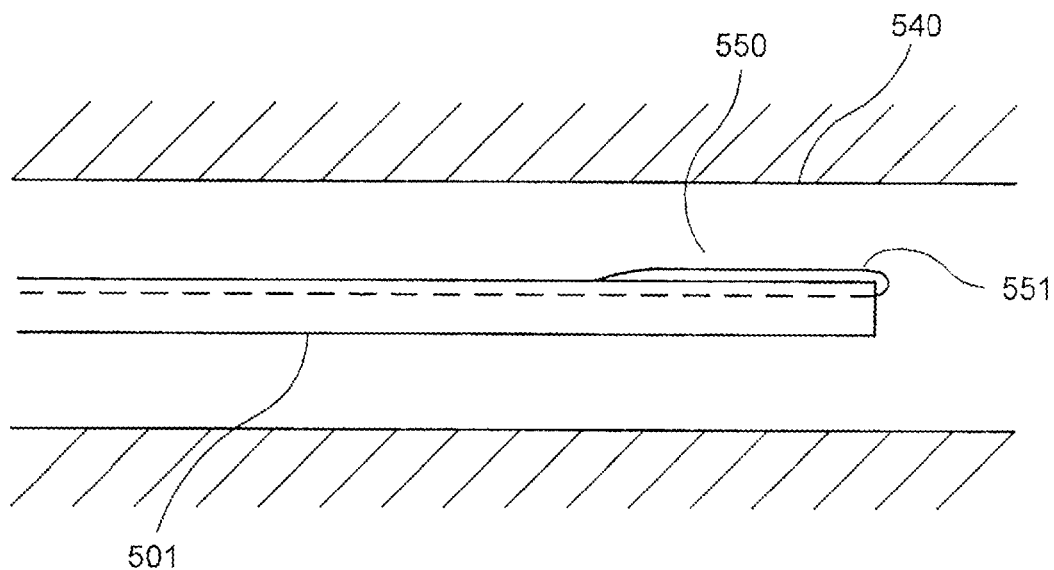
FIG. 6 shows a side view of a device according to a sixth exemplary embodiment of the present invention in position within a body lumen.
Figure 7:
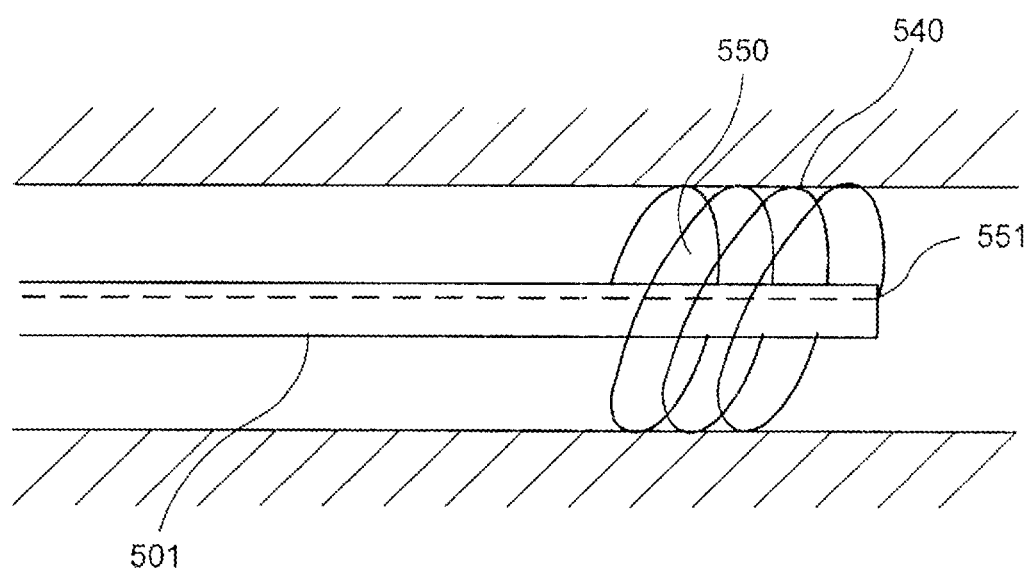
FIG. 7 shows a side view of a device according to a sixth exemplary embodiment of the present invention in position within a body lumen.

In a further embodiment, as shown in FIGS. 6 and 7, the anchoring mechanism 550 may comprise an anchoring wire 551 which extends out of an endoscope 501 via an opening 560 provided on a distal portion thereof. The anchoring wire 551 is further attached to a distal portion of the endoscope 501 at a joint portion 552. In an insertion configuration, an actuator (not shown) located on a proximal portion of the endoscope 501 may be retracted to keep a portion of the anchoring wire 551 extending between the joint portion 552 and the opening 561 constricted against the body of the endoscope 501. Accordingly, when the anchoring mechanism 550 is actuated, as shown in FIG. 7, a length of the anchoring wire may extend out of the opening 561 and may be further actuated to assume a shape memorized configuration which, in this embodiment, may be a coiled shape. In an alternate embodiment, a plurality of anchoring wires 551 may be provided wherein, when actuated, the plurality of anchoring wires 551 extend around the circumference of the endoscope 501 and provide an anchoring means on all sides thereof.

It is submitted that the features of each of the aforementioned embodiments of the present invention may be combined in any manner to create a device having desired performance characteristics without deviating from the spirit and scope of the present invention. For example, the anchoring mechanisms according to any of the disclosed embodiments of the present invention may be employed in a sterility sheath or other device through which an endoscope or other device is to be inserted to anchor the sheath in a desired location within a body lumen. Such an embodiment may add to the utility of the present invention when traversing difficult regions of the digestive tract and through other tortuous parts of the body, as those skilled in the art will understand. Those skilled in the art will understand that, although devices such as the endoscopes and sheaths described herein are often inserted into body lumens via naturally occurring body orifices, these devices may be inserted into hollow organs or body lumens via surgical openings, wounds, etc. as desired without impacting the operation of the anchoring mechanisms.

In another embodiment, the anchoring device of the present invention may be integral to an endoscope or, alternatively, can be fixedly or releasably attachable to an endoscope. Furthermore, the anchoring device need not cover the full length of the endoscope to which it is attached but rather, may alternately be attached only to a distal portion thereof. In such an embodiment, the anchoring mechanism may be actuated in a manner similar to that of the embodiments of FIGS. 1-4, wherein the actuating cable or filament may extend either outside of the endoscope or within a working channel of the endoscope. In another embodiment, the anchoring device may be integral to a sheath, wherein wires of the anchoring device may be embedded within the sheath and the distally located anchoring mechanism may extend out of the device along a distal length. As indicated above, the device of the present invention may be employed in a sterility sheath. Alternatively, any of the embodiments of the invention may be incorporated in an endoscope or other device through a surrounding sheath. In such an embodiment, the user moves the endoscope or other device through the sheath to a target location and deploys the anchoring mechanism. The anchoring mechanism pushes the flexible sheath out ward into contact with the lumenal tissue to anchor the sheath and the endoscope in place.

In yet another alternate embodiment, the device of the present invention, as described in FIGS. 3-5 may comprise any plurality of anchoring wires, wherein the increased number of wires may directly correlate to an increased gripping force exerted by the anchoring mechanism or to a more evenly distributed anchoring force, as those skilled in the art will understand.

In another alternate embodiment, the device of the present invention may employ suction to aid in anchoring the endoscope at a target site within the body. Specifically, as shown in FIG. 8, an endoscope 600 is provided with an opening 602 fluidly coupled to a suction lumen (not shown) along a lateral side of a distal portion thereof The opening 602 is sized to permit a cone 604 to extend therefrom. The cone 604 is a hollow element extending from a minimum diameter at a proximal lip 606 to a maximum diameter at a distal lip 608. The proximal lip 606 further comprises a flange 610 that flutes outward to assume a diameter greater than a diameter of the proximal lip 606. The flange 610 may preferably be permanently attached to the endoscope 600 to prevent the cone 604 from being dislodged therefrom.

The cone 604 is formed of a substantially flexible biocompatible material to permit proximal and/or distal deflection thereof during insertion to a target location in a body lumen 640. Once the target location has been reached, suction is applied at a proximal end of a lumen 614 of the endoscope 600 to cause the cone 604 to attach to a wall of the body lumen 640. A guiding device 612 is then inserted into the lumen 614 to a location extending partially laterally out of the lumen 614 and into the cone 604, as shown in FIG. 8. A guide wire 616 is actuated to extend distally out of the guiding device 612 and attach to the wall of the body lumen 640. An attachment 618 of the guide wire 616 may comprise, for example, a knot, hook, latch, or other attachment mechanism known in the art. Thus, suction applied to the cone 604 helps maintain a position of the cone 604 against the wall of the body lumen 640 while the attachment 618 of the guide wire 616 locks the endoscope and further aids in preventing longitudinal movement of the cone against the wall of the body lumen 640. The embodiment of FIG. 8 permits a centering of a position of the endoscope relative to walls of the body lumen 640. Alternatively, the cone 604 may assume any suitable dimension to permit any positioning of the endoscope 600 relative the body lumen 640, as those skilled in the art will understand.

FIG. 9 depicts another alternate embodiment of the present invention, in which a suction opening is formed through a wall of an endoscope 700. Specifically, the endoscope 700 is formed substantially similarly to the endoscope 100 with the exception of a suction window 702 formed on a portion of an outer wall thereof. The suction window 702 may be dimensioned to suit the requirement of a body lumen 740 into which the endoscope 700 is inserted. Furthermore, the suction window 702 may extend over any portion of the endoscope 700 wall without deviating from the spirit and scope of the present invention. A visualization window 704 may be formed on the endoscope 700 on a location opposite the suction window 702. The visualization window 704 may be formed as an outlet for distal ends of optical fibers extending longitudinally through the endoscope 700, as those skilled in the art will understand. Alternatively, the visualization window 704 may permit visualization of the body lumen 740 using any means known in the art. Positioning the visualization window 704 opposite the suction window 702 allows an unobstructed view of the body lumen 740 in an operative configuration. Specifically, when a suction force is applied to a proximal portion of the lumen 706 of the endoscope 700, the suction window 702 is automatically drawn into contact with an adjacent surface of the body lumen 640, thus centering the visualization window 704 therein.

The present invention has been described with reference to specific exemplary embodiments. Those skilled in the art will understand that various modifications and changes may be made to the embodiments. The specification is, therefore, to be regarded in an illustrative rather than a restrictive sense.

What is claimed is:

1. A tissue access device comprising:
   an endoscope having a lumen therethrough; and
   an anchoring member coupled to and extending from an opening on a lateral side of a distal portion of the endoscope, the anchoring member configured to deliver to a body lumen a suction force applied at a proximal end of the device, the suction force configured to cause the anchoring member to engage tissue defining the body lumen.

2. The device of claim 1, further comprising a tubular guiding component disposed in the lumen.

3. The device of claim 2, wherein the guiding component comprises a flexible distal portion configured to exit the endoscope at the opening.

4. The device of claim 2, wherein all of the anchoring member is positioned proximal to a distal-most surface of the endoscope.

5. The device of claim 1, wherein the anchoring member comprises a proximal end coupled to the opening and a distal end configured to apply the suction force to the tissue.

6. The device of claim 5, wherein a diameter of the distal end of the anchoring member is greater than a diameter of the proximal end of the anchoring member.

7. The device of claim 5, further comprising sloped side walls between the distal end of the anchoring member and the proximal end of the anchoring member.

8. The device of claim 1, wherein a proximal end of the anchoring member comprises a flange member configured to couple the anchoring member to the opening.

9. The device of claim 1, further comprising an attachment member configured to engage the tissue, wherein the attachment member is disposed through the lumen and extends through the anchoring member.

10. The device of claim 1, wherein the anchoring member extends from the opening along an axis perpendicular to a longitudinal axis of the endoscope.

11. A tissue access device comprising:
an endoscope having a lumen therethrough; and
an anchoring member configured to apply an adhesive force to body tissue, the anchoring member having a first end coupled to an opening in a sidewall of a distal portion of the endoscope and a second end configured to contact the body tissue during application of the adhesive force,
wherein the second end has a diameter greater than a diameter of the first end.

12. The device of claim 11, wherein the adhesive force is a suction force applied from a proximal end of the endoscope and through the lumen.

13. The device of claim 11, further comprising a tubular guiding component disposed in the lumen.

14. The device of claim 13, wherein a diameter of the guiding component is less than a diameter of the anchoring member.

15. The device of claim 13, further comprising an attachment member disposed in a lumen of the guiding component.

16. The device of claim 15, wherein the attachment member comprises a hook shaped distal end.

17. The device of claim 13, wherein the guiding component comprises a flexible distal portion configured to exit the endoscope at the opening.

18. The device of claim 11, further comprising a sloped side wall between the first end of the anchoring member and the second end of the anchoring member.

19. The device of claim 11, wherein the first end of the anchoring member comprises a flange member configured to couple the anchoring member to the opening.

20. A method of accessing target tissue within a body lumen comprising:
inserting a medical device at a location proximal the target tissue, wherein the medical device comprises an endoscope having a lumen therethrough, and an anchoring member coupled at a first end to an opening in a lateral side of a distal portion of the endoscope,
inserting a tubular guiding component through the lumen and out of the opening to engage a portion of the target tissue;
applying suction through the lumen to the anchoring member to cause a second end of the anchoring member to engage a surface of the target tissue,
wherein a diameter of the second end of the anchoring member is greater than a diameter of the first end of the anchoring member.

* * * * *